US006610880B1

(12) United States Patent
Overkamp et al.

(10) Patent No.: US 6,610,880 B1
(45) Date of Patent: Aug. 26, 2003

(54) PROCESS FOR PREPARING PEROXIDES USING MIXED ANHYDRIDES

(75) Inventors: Johannes Willibrordus A. Overkamp, Lemelerveld (NL); Marinus Catharinus Tammer, Schalkhaar (NL); Bernard De Vries, Harderwijk (NL); Anna Gerdine Van De Bovenkamp-Bouwman, Nijkerk (NL)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/686,785

(22) Filed: Oct. 11, 2000

Related U.S. Application Data
(60) Provisional application No. 60/171,409, filed on Dec. 21, 1999.

(30) Foreign Application Priority Data

Oct. 13, 1999 (EP) .............................................. 99203364

(51) Int. Cl.$^7$ ........................................... C07C 409/38
(52) U.S. Cl. ..................................................... 560/302
(58) Field of Search ........................................ 560/302

(56) References Cited

U.S. PATENT DOCUMENTS

| 2,567,615 | A | * | 9/1951 | Milas et al. | |
| 3,138,627 | A |   | 6/1964 | Harrison et al. | 260/453 |
| 3,190,904 | A | * | 6/1965 | Spoors et al. | |
| 3,352,926 | A |   | 11/1967 | Guillet et al. | 260/610 |
| 3,435,060 | A |   | 3/1969 | Johannes | 260/435 |
| 3,595,898 | A | * | 7/1971 | Harvey et al. | |
| 4,219,676 | A | * | 8/1980 | Sanchez et al. | 568/566 |
| 5,117,047 | A | * | 5/1992 | Suyama et al. | 560/302 |

FOREIGN PATENT DOCUMENTS

| DE | 1 518 740 | 6/1972 | ........... C07C/73/00 |
| EP | 0 126 216 | 11/1984 | ......... C07C/179/18 |
| EP | 0 133 554 | 2/1985 | ......... C07C/179/15 |
| WO | WO 99/32442 | 7/1999 | ......... C07C/407/00 |
| WO | WO 99/52864 | 10/1999 | ......... C07C/407/00 |

OTHER PUBLICATIONS

CA:114:62976 abs of EP381135 Aug. 1990.*
CA:79:52634 abs of Zh. Fiz. Khim. by Turovskii et alt 47(1) pp. 9–12 1973.*

*Chemical Abstract XP–00212108*, Iwasaki, Shuichi; Date, Atsushi; Nomaguchi, Makto, 1995.
*Chemical Abstract XP–002142112*, Stankevich, A. I.; Zyat'kov, I. P.; Lazareva, A. M.; El'nitskii, A. P., 1981.
*Chemical Abstract XP–002142109*, Nosan, V. N., 1975.
John T. Barbas and J. E. Leffler, *The Decomposition of Phenolic Peresters. II. tert–Butyl3, 5–Di–tert–butyl–2–hydroxyperbenzoate and tert–Butyl5–Methyl–3–tert–butyl–2–hydroxyperbenzoate$^1$*, Journal of the American Chemical Society vol. 97, No. 25, 1975, pp. 7270–7272.
Richard S. Glass and Jeffrey L. Broeker, *Formation of Sulfur–Centered Cation Radicals by Photofragmentation Tetrahedron Letter*, vol. 33, No. 13, 1992, pp. 1721–1724.
*Chemical Abstract XP–00214211*, Turovskii, A. A.; Kucher, R. V.; Titov, E. V,; Belobrov, V. M.; Serdyuk A. I. Ustinova, A. M., 1973.
*Chemical Abstract XP–002142110*, Simionescu, C. I.,; Dumitriu, S,; Bouzaher, Y., 1982.

* cited by examiner

*Primary Examiner*—Jean F. Vollano
(74) *Attorney, Agent, or Firm*—Richard P. Fennelly

(57) ABSTRACT

The invention relates to a process for the preparation of a peracid, perester or diacylperoxide and is characterized in that a mixed anhydride of formula $R^1[C(O)OC(O)OR^2]_n$ or $[R^3C(O)OC(O)O]_pR^4$ is contacted with a hydroperoxide of formula $R^5[OOH]_m$ in the presence of a base, wherein $R^1$ represents a mono-, di-, tri- or tetravalent $C_1$–$C_{19}$ hydrocarbon group, optionally containing one or more hetero atoms, n is 1–4, $R^2$ represents a $C_1$–$C_{20}$ hydrocarbon group, optionally containing one or more hetero atoms, $R^3$ represents a $C_1$–$C_{19}$ hydrocarbon group, optionally containing one or more hetero atoms, $R^4$ represents a di-, tri- or tetravalent $C_1$–$C_{20}$ hydrocarbon group, optionally containing one or more hetero atoms, p is 2–4, $R^5$ represents hydrogen or a mono- or divalent $C_3$–$C_{18}$ tertiary alkyl or $C_2$–$C_{20}$ acyl group, in which the tertiary alkyl or acyl group may optionally contain one or more hetero atoms, m is 1 or 2, and if $R^5$ represents hydrogen, m is 1, provided that if the hydroperoxide is an α,α'-dihydroperoxyperoxide, the reaction is not carried out in an inert two-phase solvent system comprising a polar solvent and an apolar solvent. The invention also relates to a hydroxyperacid, hydroxyperester, and hydroxydiacylperoxide obtainable by said process and the use of said hydroxyperoxides.

12 Claims, No Drawings

PROCESS FOR PREPARING PEROXIDES USING MIXED ANHYDRIDES

This application claims priority from European patent Application No. 99203364.7, filed Oct. 13, 1999 and also claims the benefit of U.S. Provisional Application Serial No. 60/171,409, filed Dec. 21, 1999.

FIELD OF THE INVENTION

The invention relates to a process for preparing a peracid, perester or diacylperoxide, a hydroxyperacid, hydroxyperester, and hydroxydiacylperoxide obtainable by said process, and the use of said hydroxyperoxides.

BACKGROUND OF THE INVENTION

Peracids, peresters, and diacylperoxides are commercially important compounds and are used in bleaching, oxidation and/or epoxidation reactions (e.g. m-chloroperbenzoic acid) and/or as chain transfer agents and/or initiators for the radical (co)polymerization of (ethylenically unsaturated) monomers into polymers, e.g., (meth)acrylic resins, polyethylenes, polyvinylchlorides, polystyrenes, and copolymers thereof. These peroxides are also used for the modification of said polymers, e.g., grafting of monomers onto polymers, degradation or molecular weight reduction of polymers, and cross-linking. They may also be used for curing unsaturated polyesters. These peroxides can be used as such or in the form of a solution, emulsion or suspension containing the peroxide. Various methods of synthesis of the aforementioned peroxides are known in the art. Most of the reported methods and in particular the commercial routes involve the use of an acid chloride or an anhydride such as acetic anhydride or phthalic anhydride and sometimes a solvent.

These prior art methods suffer from the disadvantage that acid chlorides are expensive starting materials. Furthermore, some of the acid chlorides which would have to be used for the synthesis of the peroxides in accordance with the present invention have a very bad smell or have no EINECS (Europe), ELINCS (Europe), ENCS (Japan), and/or TSCA (United States) registration, which of course limits their use on a technical scale. Further, functionalized carboxylic acids of which the functional group reacts with an acid chloride group cannot be converted into the corresponding peroxides via the acid chloride route either. The use of anhydrides has the drawback that one equivalent of the corresponding acid is formed. Hence, this route is unattractive if the use of an expensive carboxylic acid is required.

For these reasons there is a need in this art for an alternate, preferably improved method of preparing peracids, peresters, diacylperoxides, and functionalized derivatives thereof.

We have found a new, commercially attractive process for preparing peracids, peresters, diacylperoxides, and functionalized derivatives thereof, which process does not suffer from the above-mentioned disadvantages.

SUMMARY OF THE INVENTION

The present invention generally relates to a process for preparing a peracid, perester or diacylperoxide, a hydroxyperacid, hydroxyperester, and hydroxydiacylperoxide obtainable by said process, and the use of said hydroxyperoxides. The process according to the present invention is characterized in that a mixed anhydride of specific formula is contacted with a hydroperoxide of formula of specific formula in the presence of a base, provided that if the hydroperoxide is an $\alpha,\alpha'$-dihydroperoxyperoxide, the reaction is not carried out in an inert two-phase solvent system comprising a polar solvent and an apolar solvent.

DETAILED DESCRIPTION OF THE INVENTION

As previously described, the present invention generally relates to a process for preparing a peracid, perester or diacylperoxide, a hydroxyperacid, hydroxyperester, and hydroxydiacylperoxide obtainable by said process, and the use of said hydroxyperoxides. The process according to the present invention is characterized in that a mixed anhydride of formula $R^1[C(O)OC(O)OR^2]_n$ or $[R^3C(O)OC(O)O]_pR^4$ is contacted with a hydroperoxide of formula $R^5[OOH]_m$ in the presence of a base, wherein $R^1$ represents a mono-, di-, tri- or tetravalent $C_1$–$C_{19}$ hydrocarbon group, optionally containing one or more hetero atoms, n is 1–4, $R^2$ represents a $C_1$–$C_{20}$ hydrocarbon group, optionally containing one or more hetero atoms, $R^3$ represents a $C_1$–$C_{19}$ hydrocarbon group, optionally containing one or more hetero atoms, $R^4$ represents a di-, tri- or tetravalent $C_1$–$C_{20}$ hydrocarbon group, optionally containing one or more hetero atoms, p is 2–4, $R^5$ represents hydrogen or a mono- or divalent $C_3$–$C_{18}$ tertiary alkyl or $C_2$–$C_{20}$ acyl group, in which the tertiary alkyl or acyl group may optionally contain one or more hetero atoms, m is 1 or 2, and if $R^5$ represents hydrogen, m is 1, provided that if the hydroperoxide is an $\alpha,\alpha'$-dihydroperoxyperoxide, the reaction is not carried out in an inert two-phase solvent system comprising a polar solvent and an apolar solvent.

In Applicant's non-prepublished International Patent Application No. PCT/EP99/02643—later published as WO 99/52864—a process for preparing inter alia monoperoxy esters is described comprising reacting an $\alpha,\alpha'$-dihydroperoxyperoxide (referred to in the publication as a type-3 ketone peroxide) with a reactive carbonyl compound, which may be a mixed anhydride, in an inert two-phase solvent system comprising a polar solvent and an apolar solvent. The $\alpha,\alpha'$-dihydroperoxyperoxides described therein are of the formula $HOOC(R^a)(R^b)OOC(R^a)(R^b)OOH$, wherein $R^a$ and $R^b$ are independently selected from the group consisting of hydrogen and $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl groups, or $R^a$ and $R^b$ form a $C_3$–$C_{12}$ cycloalkyl group, which groups may include linear or branched alkyl moieties, and each of $R^a$ and $R^b$ may optionally be substituted with one or more groups selected from hydroxy, alkoxy, linear or branched alkyl, aryloxy, halogen, ester, carboxy, nitrile, and amido groups.

The present invention further relates to new hydroxyperacids, hydroxyperesters, and hydroxydiacylperoxides obtainable by the process defined above. Said hydroxyperoxides are further described below.

For illustrating the process in accordance with the present invention, the following reaction schemes are presented:

$R^1C(O)OC(O)OR^2 + HOOH$ gives $R^1C(O)OOH$, a peracid $R^1C(O)OC(O)OR^2 + HOOH$ gives $R^1C(O)OOC(O)R^1$, a diacylperoxide $R^1C(O)OC(O)OR^2$+tert-alkylOOH gives $R^1C(O)OO$tert-alkyl, a perester $R^1C(O)OC(O)OR^2$+acylOOH gives $R^1C(O)OO$acyl, a diacylperoxide $R^1C(O)OC(O)OR^2+R^5(OOH)_2$ gives $R^1C(O)OOR^5OOH$, a ketone peroxide 2 $R^1C(O)OC(O)OR^2+R^5(OOH)_2$ gives $R^1C(O)OOR^5OOC(O)R^1$, a ketone diperester, 2 Tert-alkylOOC(O)$R^1$C(O)OC(O)OR$^2$+HOOH gives a diacylperoxide having perester groups: tert-alkylOOC(O)$R^1$C(O)OOC(O)$R^1$C(O)OOtert-alkyl.

The Mixed Anhydride

In the process according to the present invention a mixed anhydride of formula $R^1[C(O)OC(O)OR^2]_n$ or $[R^3C(O)OC(O)O]_pR^4$ is contacted with a hydroperoxide of formula $R^5[OOH]_m$ in the presence of a base. Preferably, a mixed anhydride of formula $R^1[C(O)OC(O)OR]_n$ is used in the process of the invention.

$R^1$ represents a mono-, di-, tri- or tetravalent $C_1$–$C_{19}$ hydrocarbon group (i.e. n is 1–4), optionally containing one or more hetero atoms. $R^1$ thus may contain 1, 2, 3 or 4 —C(O)OC(O)OR$^2$ (mixed anhydride) groups. Preferably, n is 1 or 2, more preferably 1.

$R^1$, $R^2$, $R^3$, $R^4$, and $R^5$ independently may contain one or more hetero atoms (although the group $R^5$ does not form part of a mixed anhydride this aspect of its definition nevertheless is discussed here in this section of the application). Suitable hetero atoms include oxygen, nitrogen, and halogen atoms, with oxygen and halogen atoms being preferred. The one or more hetero atoms may form functional groups in addition to the mixed anhydride group such as an ether, hydroxy, alkoxy, aryloxy, carbonyl, carboxy (i.e. acid, ester), peroxyester, percarbonate, nitrile, or amido group. Preferred functional groups are ether, hydroxy, carbonyl, and carboxy groups. More preferred are hydroxy groups. Preferably, the halogen atom is a chlorine or bromine atom, more preferably a chlorine atom.

Preferably, $R^1$, $R^2$, $R^3$, $R^4$, and $R^5$ independently only contain a single functional group. More preferably, $R^1$, $R^3$, and $R^5$ independently contain one or more hydroxy groups, even more preferably one hydroxy group. These R groups independently may further contain other functional groups as described above. Still more preferably, $R^1$, $R^3$ and $R^5$ independently only contain a hydroxy group as the sole functional group. Most preferably, $R^1$ or $R^3$ and $R^5$ contain a single hydroxy group.

Suitable $R^1$ groups include $C_1$–$C_{19}$ alkyl, $C_3$–$C_{19}$ cycloalkyl, $C_3$–$C_{19}$ cycloalkylalkyl, $C_6$–$C_{19}$ aryl, $C_7$–$C_{19}$ arylalkyl, and $C_7$–$C_{19}$ alkylaryl groups, optionally containing one or more hetero atoms as defined above, wherein the alkyl moieties may be linear or branched, saturated or unsaturated, and the aryl moieties may be substituted with one or more substituents or not. Preferred substituents are hydroxy groups, linear or branched $C_1$–$C_4$ alkyl groups, and halogen atoms, more preferably hydroxy groups, methyl groups, and chlorine atoms. Preferably, $R^1$ represents a linear or branched C:$_4$–$C_{12}$ alkyl group or a $C_6$–$C_{12}$ aryl group, said alkyl and aryl groups optionally being substituted with a hydroxy group, a linear or branched $C_1$–$C_4$ alkyl group such as a methyl group or a halogen atom such as a chlorine atom.

The process in accordance with the present invention is particularly suitable for preparing hydroxyperacids, hydroxyperesters, and hydroxydiacylperoxides having a hydroxy group in $R^1$ or $R^3$, more in particular hydroxyperesters and hydroxydiacylperoxides having a hydroxy group in $R^1$ or $R^3$ and having a hydroxy group in $R^5$.

Hence, the invention further relates to hydroxyperacids obtainable by the process described above wherein $R^1$ or $R^3$ represents a $C_1$–$C_{19}$ hydrocarbon group, optionally containing one or more hetero atoms, substituted with a hydroxy group, n, $R^2$, $R^4$, and p have the meaning defined above, $R^5$ represents hydrogen, and m is 1. Preferably, said hydroxyperacid is substituted with a single hydroxy group.

The invention also relates to hydroxyperesters obtainable by the process described above wherein $R^1$ or $R^3$ represents a $C_3$–$C_{20}$ hydrocarbon group, optionally containing one or more hetero atoms, substituted with a hydroxy group, n, $R^2$, $R^4$, and p have the meaning defined above, $R^5$ represents a mono- or divalent $C_3$–$C_{18}$ tertiary alkyl group, optionally containing one or more hetero atoms, optionally substituted with a hydroxy group, and m is 1 or 2, with the exception of (9Z, 12R) 12-hydroxy-9-octadeceneperoxoic acid 1,1-dimethylethyl ester, 4-[(1,3-dihydro-1-hydroxy-3-oxo-2H-inden-2-ylidene)methyl]benzenecarboperoxoic acid 1,1-dimethylethyl ester, 4-(2-hydroxypropoxy)-4-oxo-butaneperoxoic acid 1,1-dimethylethyl ester, (1-hydroxy-1-methylethyl)-butanediperoxoic acid bis(1,1-dimethylethyl) ester, 6-(2-hydroxyethoxy)-6-oxo-hexaneperoxoic acid 1,1'-(1,1,3-trimethyl-1,3-propanediyl)ester, and 3,4-dihydroxycyclohexenecarboperoxoic acid 1,1-dimethylethyl ester, with the proviso that said hydroxyperester does not contain a hydroxyphenyl moiety or a 2-hydroxypropyl group and the hydroxy group is not in the form of a carboxylic acid group.

Preferably, n is 1 or 2. Preferably, $R^1$ or $R^3$ represents a $C_3$–$C_{12}$ hydrocarbon group. Preferably, $R^5$ represents a monovalent $C_3$–$C_{19}$ tertiary alkyl group, more preferably a monovalent $C_3$–$C_{12}$ tertiary alkyl group. It is preferred that—apart from the perester group—the hydroxy group is the only functional group present in the molecule. Particularly preferred hydroxyperesters are those which have a single hydroxy group in $R^1$ or $R^3$ as well as in $R^5$.

The invention further relates to hydroxydiacylperoxides obtainable by the process described above wherein $R^1$ or $R^3$ represents a $C_1$–$C_{19}$ hydrocarbon group, optionally containing one or more heteroatoms, substituted with a hydroxy group, n, $R^2$, $R^4$, and p have the meaning defined above, $R^5$ represents hydrogen or a mono- or divalent $C_2$–$C_{20}$ acyl group, said acyl group optionally containing one ore more hetero atoms, said acyl group optionally substituted with a hydroxy group, and m is 1 or 2, with the exception of benzoyl hydroxyacetylperoxide, with the proviso that said hydroxydiacylperoxide does not contain a hydroxyphenyl moiety.

Preferably, n is 1 or 2. Preferably, $R^1$ or $R^3$ represents a $C_1$–$C_{12}$ hydrocarbon group. Preferably, $R^5$ represents a monovalent $C_1$–$C_{12}$ acyl group, more preferably a monovalent $C_2$–$C_{12}$ acyl group. Most preferably, $R^5$ represents. hydrogen. It is preferred that—apart from the diacylperoxy group—the hydroxy group is the only functional group present in the molecule. Particularly preferred hydroxydiacylperoxides are those which have a single hydroxy group in both acyl moieties.

Peroxides containing an aromatic hydroxy group, e.g., 4-hydroxyperbenzoic acid, typically are not suitable for use in radical reactions. However, they may be used in other applications. In contrast, the corresponding hydroxyalkylaryl derivatives, for example, can be used in all applications listed above.

Typical examples of carboxylic acids from which the $R^1[C(O)O—]_n$ moiety of the mixed anhydride of formula $R^1[C(O)OC(O)OR^2]_n$ is derived (as described below) include monoacids (i.e. n is 1) such as acetic acid, chloroacetic acid, dichloroacetic acid, propanoic acid, 2-methylpropionic acid, 2-methylbutanoic acid, propenoic acid, acrylic acid, methacrylic acid, butanoic acid, 2-butenoic acid, 2-methyl-2-butenoic acid, 3-methyl-2-butenoic acid, 2,3-dimethyl-2-butenoic acid, 2-ethyl-2-butenoic acid, 3-phenylpropenic acid, 2,2-dimethylpropanoic acid, 2,2-dimethylbutanoic acid, 2,2-dimethylpentanoic acid, 2-ethylbutanoic acid, 3,5,5-trimethylhexanoic acid, 2-ethylhexanoic acid, neohexanoic acid, 2-pentenoic acid, 4-methyl-2-pentenoic acid, 2,3-dimethyl-2-pentenoic acid, 3,4-dimethyl-2-2-pentenoic acid, 2-hexenoic acid, 2,4-hexadienoic acid, neoheptanoic acid, 2-octenoic acid, 2-nonenoic acid, neodecanoic acid, octanoic acid, nonanoic acid, lauric acid, benzoic acid, 2-methylbenzoic acid, 3-methylbenzoic acid, 4-methylbenzoic acid, 4-tert-butylbenzoic acid, 3-chlorobenzoic acid, 2,4-dichlorobenzoic acid, p-phenylenediacrylic acid, 3-benzoylacrylic acid, phenylacetic acid, phenoxyacetic acid, cyclohexanecarboxylic acid, 3-hydroxybutanoic acid, 4-hydroxybutanoic acid, 2-hydroxypentanoic acid, 3-hydroxypentanoic acid, 4-hydroxypentanoic acid, 5-hydroxypentanoic acid, 4-hydroxy-2-pentenoic acid, hydroxyacetic acid, 2-hydroxyisobutyric acid, 2-hydroxypropanoic acid, 2-hydroxyhexanoic acid, 6-hydroxyhexanoic acid, 8-hydroxyoctanoic acid, hydroxypivalic acid; diacids (i.e. n is 2) such as succinic acid, methylsuccinic acid, diglycolic acid, glutaric (i.e. pentanedioic)acid, 3,5,5-trimethylpentanedioic acid, hexanedioic acid, 3,5,5-trimethylhexanedioic acid, 2,4,4-trimethylhexanedioic acid, decanedioic acid, undecanedioic acid, dodecanedioic acid, 1,4-cyclohexanedicarboxylic acid, cyclohexane-1,4-diacetic acid, maleic acid, citraconic acid, itaconic acid, fumaric acid, oxalic acid, terephthalic acid, phthalic acid, and isophthalic acid, hydroxysuccinic acid; triacids (i.e. n is 3) such as citric acid, 1,2,4-benzenetricarboxylic acid, and 1,3,5-benzenetricarboxylic acid; and tetraacids (i.e. n is 4) such as 1,2,4,5-benzenetricarboxylic acid and ethylenediaminetetraacetic acid.

Mixtures of one or more carboxylic acids may also be used for preparing the mixed anhydride. It is further noted that for some of the above-mentioned functionalized carboxylic acids suitable precursors are commercially available, e.g., 6-hydroxyhexanoic acid or its alkali metal salt may be prepared from the corresponding lactone following methods known to a skilled person. Ethyl 3-hydroxybutanoate can be used to prepare sodium 3-hydroxybutanoate and without removal of ethanol, the sodium salt can be converted into a mixed anhydride as described below.

If a di-, tri- or tetravalent carboxylic acid is used as the starting material it is not necessary to convert all carboxylic acid groups. Hence, by using such higher carboxylic acids, carboxylic acid groups could be introduced into the peroxides in accordance with the present invention. Mono- and diacids are preferred.

$R^2$ represents a $C_1$–$C_{20}$ hydrocarbon group, optionally containing one or more hetero atoms (see above). Preferably, $R^2$ represents a $C_3$–$C_8$ alkyl or a $C_6$–$C_{12}$ aryl group, most preferably a $C_3$–$C_4$ secondary alkyl group or a phenyl group.

The —$C(O)OR^2$ moiety of the mixed anhydride of formula $R^1[C(O)OC(O)OR^2]_n$ is derived from a halogen formate, preferably a chloroformate.

Typical examples of chloroformates include 1-methylpropyl chloroformate, 4-methylphenyl chloroformate, phenyl chloroformate, 3-methoxybutyl chloroformate, phenylmethyl chloroformate, 2-methylphenyl chloroformate, 1,3-dimethylbutyl chloroformate, 3,4-dimethylbutyl chloroformate, octyl chloroformate, ethyl chloroformate, 2-methylpropyl chloroformate, n-butyl chloroformate, 2-ethylhexyl chloroformate, 2-methyl-2-propenyl chloroformate, cyclohexyl chloroformate, 3,5,5-trimethylhexyl chloroformate, methyl chloroformate, 2-methoxyethyl chloroformate, 1-methylethenyl chloroformate, diethyleneglycol bis (chloroformate), 2-ethoxyethyl chloroformate, 4-methoxy carbophenyl chloroformate, 1-methylethyl chloroformate, pentyl chloroformate, hexyl chloroformate, n-propyl chloroformate, 2,2-dimethylpropyl chloroformate, 1,1-dimethylethyl chloroformate, 1-methylheptyl chloroformate, and mixtures thereof.

Particularly preferred and inexpensive chloroformates are isopropyl chloroformate, sec-butyl chloroformate, and phenyl chloroformate.

$R^3$ represents a $C_1$–$C_{19}$ hydrocarbon group, optionally containing one or more hetero atoms (see above). $R^3$ has the same (preferred) definitions as are described above for $R^1$ in the case of a monovalent (i.e. n is 1) $C_1$–$C_{19}$ hydrocarbon group. The $R^3C(O)O$— moiety of the mixed anhydride of formula $[R^3C(O)OC(O)O]_pR^4$ is derived from a carboxylic monoacid and suitable examples have been described above. $R^4$ represents a di-, tri- or tetravalent (i.e. p is 2–4) $C_1$–$C_{20}$ hydrocarbon group, optionally containing one or more hetero atoms (see above). The [—$C(O)O]_pR^4$ moiety of the mixed anhydride of formula $[R^3C(O)OC(O)O]_pR^4$ is derived from a bis- tris- or tetra(halogen formate), preferably the corresponding chloroformate. Preferably, p is 2 and a bischloroformate is used in the invention process.

Typical examples of suitable bischloroformates include ethylene glycol bischloroformate, diethylene glycol bischloroformate, triethylene glycol bischloroformate, 2,2-dimethyl-1,3-propanediol bischloroformate, bisphenol A bischloroformate, 1,4-butanediol bischloroformate, 1,6-hexanediol bischloroformate, 1,4-cyclohexanedimethanol bischloroformate, and 3-methyl-1,5-pentanediol bischloroformate.

A preferred readily available bischloroformate is diethylene glycol bischloroformate.

A typical example of a trischloroformate is tris (chlorocarbonyloxymethyl)ethane and of a tetrachloroformate is tetra(chlorocarbonyloxymethyl)methane (i.e. pentaerythritol tetrachloroformate).

Typical examples of mixed anhydrides which can be used in the process according to the invention include 3-chlorobenzoyl 1-methyl-1-propyl carbonate, phenoxyacetyl 1-methyl-1-propyl carbonate, 6-hydroxyhexanoyl 1-methylethyl carbonate, 4-methylbenzoyl 1-methyl-1-propyl carbonate, and cyclohexylcarbonyl 1-methyl-1-propyl carbonate.

Preparation of the Mixed Anhydride

The mixed anhydride of formula $R^1[C(O)OC(O)OR^2]_n$ or $[R^3C(O)OC(O)O]_pR^4$ may be prepared according to methods that are well-known to a person skilled in the art.

In a preferred embodiment of the invention process—which is described in more detail below—the mixed anhydride used in the invention process is prepared in an aqueous medium. According to this embodiment, the mixed anhydride is prepared by reacting a carboxylic acid of formula $R^1[C(O)OH]_n$ with a halogen formate, preferably a chloroformate of formula $XC(O)OR^2$ or a bischloroformate of formula $[XC(O)O]_2R^4$, in the presence of a base in an aqueous medium, wherein $R^1$, $R^2$, $R^4$, n, and p have the same meaning as defined above and X is a halogen atom. Suitable examples of carboxylic acids and halogen formates are described above.

The reaction can be carried out using means and equipment that are known to one of ordinary skill in the art. It can be carried out in a batch, semi-batch or continuous fashion.

It was found that the carboxylic acid should not be too acidic. For example, the mixed anhydride of oxalic acid (i.e. $pKa_1$ of 1.23 and $pKa_2$ of 4.19) could not be detected or isolated when prepared in an aqueous medium. Preferably, a carboxylic acid having a (first) pKa of 3 or higher, more preferably 4 or higher is used.

It is to be noted that in particular hydroxy-containing carboxylic acids, which are able to form a 5- or 6-membered ring lactone, are less suitable starting materials for making a mixed anhydride in an aqueous medium.

Any base can be used for making the mixed anhydride in an aqueous medium. Suitable bases include alkali metal hydroxides such as lithium hydroxide, sodium hydroxide, potassium hydroxide, alkaline earth metal hydroxides such as magnesium hydroxide and calcium hydroxide, sodium carbonate, sodium bicarbonate, sodium phosphate, sodium hydrogen phosphate, calcium oxide, magnesium oxide, and mixtures thereof. Preferably, sodium hydroxide, potassium hydroxide, sodium carbonate, sodium phosphate or a mixture thereof is used as the base, most preferably sodium hydroxide or potassium hydroxide. Typically, an aqueous solution of the base is used.

Typically, the pH during the preparation of the mixed anhydride in an aqueous medium is kept at a value of 3 to 14, preferably 5 to 11, most preferably 6 to 9.

The molar ratio of carboxylic acid to halogen formate can vary over a wide range. Preferably, about equimolar amounts of carboxylic acid and halogen formate are used.

The preparation of the mixed anhydride in an aqueous medium can be carried out within a wide temperature range, typically from −25 o 75° C. Preferably, the reaction is carried out at −10 to 40° C., most preferably 0 to 20° C.

Typically, the reaction time in a batch process ranges from 0.1 to 10 h. Suitably, the reaction time is from 0.5 to 3 reaction times generally are shorter.

Although the preparation of the mixed anhydride in an aqueous medium can be carried out without the use of a catalyst, it is advantageous to use one. Typically, a phase transfer catalyst is used as a suitable catalyst. Preferably, the phase transfer catalyst is a quaternary ammonium compound. Said quaternary ammonium phase transfer catalysts are known in the art. Typical examples include tetrabutylammonium bromide, benzyltrimethylammonium chloride, methyltricaprylammonium chloride, methyltributylammonium chloride, methyltrioctylammonium chloride, triethylbenzylammonium chloride, cocobenzyldimethylammonium chloride, and tetrabutylammonium hydrosulphate. However, tertiary amines such as triethylamine, trimethylamine, and N-methylmorpholine can also be used.

Typically, the quaternary ammonium phase transfer catalyst is used in an amount of 0.01 to 10 mole %, preferably 0.1 to 3 mole %, based on the amount of carboxylic acid.

The Hydroperoxide $R^5$ represents hydrogen or a mono- or divalent (i.e. m is 1 or 2) $C_3$–$C_{18}$ tertiary alkyl or $C_2$–$C_{20}$ acyl group, in which the tertiary alkyl or acyl group may optionally contain one or more hetero atoms as defined above. Preferably, $R^5$ represents hydrogen or a monovalent $C_3$–$C_{18}$, more preferably $C_3$–$C_{10}$ tertiary alkyl group. The tertiary alkyl group may contain further branches, unsaturated groups such as alkynylene groups, and saturated or unsaturated rings such as cyclohexylene and phenylene groups. In the hydroperoxide of formula $R^5[OOH]_m$, the one or more hetero atoms may, in addition to forming functional groups as described above, also form peroxy or hydroperoxy groups.

If $R^5$ is hydrogen, m is 1 and the hydroperoxide to be used in the invention process is hydrogen peroxide. Typically, an aqueous solution of hydrogen peroxide is used, for example, a 50 wt % aqueous solution of hydrogen peroxide.

Typical examples of tertiary hydroperoxides which can be used in the invention process include monohydroperoxides (i.e. m is 1) such as tert-butyl hydroperoxide, 1,1-dimethylpropyl (or tert-amyl)hydroperoxide, 1,1-dimethylbutyl (or tert-hexyl)hydroperoxide, 1-methyl-1-ethylpropyl hydroperoxide, 1,1-diethylpropyl hydroperoxide, 1,1,2-trimethylpropyl hydroperoxide, cumyl hydroperoxide, 1,1-dimethyl-3-hydroxybutyl (or hexylene glycol)hydroperoxide, 1,1-dimethyl-3-(2-hydroxyethoxy) butyl hydroperoxide, 1,1-dimethyl-3-(2-hydroxy-1-propyloxy)butyl hydroperoxide, 1,1-dimethyl-3-(1-hydroxy-2-propyloxy)butyl hydroperoxide, 1,1-dimethylpropenyl hydroperoxide, and 1,1,3,3-tetramethylbutyl hydroperoxide and dihydroperoxides (i.e. m is 2) such as 2,2-dihydroperoxypropane, 2,5-dimethyl-2, 5-dihydroperoxyhexane, 2,5-dimethyl-2,5-dihydroperoxyhex-3-yne, 1,3-cyclohexylenedi(1-methylethylidenehydroperoxide), 1,4-cyclohexylenedi(1-methylethylidenehydroperoxide), 1,3-phenylenedi(1-methylethylidenehydroperoxide), and 1,4-phenylenedi(1-methylethylidenehydroperoxide).

Typical examples of hydroperoxides in which $R^5$ represents an acyl group include perlauric acid, m-chloroperbenzoic acid, and perhexanoic acid.

Typical examples of hydroperoxides containing a second hydroperoxy group and a peroxy group are α,α'-dihydroperoxyperoxides of formula $HOOC(R^a)(R^b)OOC(R^a)(R^b)OOH$. Said peroxides are described in Applicant's non-prepublished International Patent Application No. PCT/EP99/02643 and a description of the $R^a$ and $R^b$ groups is given above. These peroxides are also referred to as ketone peroxides.

Typical examples of hydroperoxides containing a second hydroperoxy group are gem-dihydroperoxides of formula $HOOC(R^a)(R^b)OOH$, wherein $R^a$ and $R^b$ have the meaning described above. Said peroxides are known in the art and have been described, for example, in Applicant's WO 99/32442. Said peroxides are also prepared from ketones.

Suitable ketones that can be used for making said bishydroperoxides include acetone, methoxy acetone, methylchloromethyl ketone, methylbromomethyl ketone, methylethyl ketone, methyl n-propyl ketone, methylisopropyl ketone, methyl n-butyl ketone, methylisobutyl ketone, methyl tert-butyl ketone, methyl n-amyl ketone, methylisoamyl ketone, methylhexyl ketone, methylheptyl ketone, ethylpropyl ketone, ethylbutyl ketone, ethylamyl ketone, diethyl ketone, dipropyl ketone, diisobutyl ketone, isobutylheptyl ketone, 4-hydroxy4-methyl-2-pentanone, cyclohexanone, 2-methylcyclohexanone, 2,4,4-trimethylcyclohexanone, butyl levulinate, ethyl acetoacetate, methylbenzyl ketone, acetophenone (i.e. phenylmethyl ketone), and phenylethyl ketone.

Methods for the synthesis of the above-mentioned hydroperoxides are well-known in the art. Frequently, mixtures of peroxides are obtained which can be separated or used as such.

If possible, the tert-alkyl hydroperoxide is used in the process according to the present invention in the form of an aqueous solution, for example, 70 wt % aqueous tert-butyl hydroperoxide.

Peroxides that can be Obtained

Specific examples of peroxides which can be prepared by the process according to the present invention include peracids such as m-chloroperbenzoic acid; peresters such as 2,5-bis(2-ethylhexanoylperoxy)-2,5-dimethylhexane, tert-butylperoxy 2-ethylhexanoate, tert-butylperoxy m-chlorobenzoate, tert-butylperoxy o-methylbenzoate, tert-butylperoxy phenylacetate, 1,4-bis(tert-butylperoxycarbo) cyclohexane, 3-hydroxy-1,1-dimethylbutylperoxy 6-hydroxyhexanoate, 2,2,4,4-tetramethylbutylperoxy phenoxyacetate, di-tert-butylperoxy oxalate, tert-butylperoxy 2-chloroacetate, tert-butylperoxy cyclododecyloxalate, tert-butylperoxy n-butyloxalate, 1-hydroxyperoxy-1-methylpropyl, (1-methyl-1-phenylacetylperoxy)propyl peroxide; diperesters such as di((1-methyl-1-phenyl-acetylperoxy)propyl)peroxide, and 2,2-di(phenoxyacetylperoxy)-4-methylpentane; and diacylperoxides such as dicyclohexylcarbonylperoxide, di(4-methylbenzoyl)peroxide, lauroyl cyclohexylcarbonyl peroxide, and lauroyl 6-hydroxyhexanoyl peroxide.

Specific examples of new hydroxy-containing peroxides in accordance with the present invention include hydroxyperacids such as 3-hydroxyperbenzoic acid and 4-hydroxyperbenzoic acid; hydroxyperesters such as tert-butylperoxy 6-hydroxyhexanoate, tert-amylperoxy 6-hydroxyhexanoate, 3-(2-hydroxyethoxy)-1,1-dimethylbutylperoxy 6-hydroxyhexanoate, tert-butylperoxy 3-hydroxybutanoate, tert-amylperoxy 3-hydroxybutanoate, 3-hydroxy-1,1-dimethylbutylperoxy 3-hydroxybutanoate, 3-(2-hydroxyethoxy)-1,1-dimethylbutylperoxy 3-hydroxybutanoate, 3-hydroxy-1,1-dimethylbutylperoxy 4-hydroxybutanoate, 1,1-dimethylpropylperoxy 3-hydroxypentanoate, 1,1,4,4-tetramethylbutylperoxy 4-hydroxypentanoate, 3-hydroxy-1,1-dimethylbutylperoxy 5-hydroxypentanoate, cumylperoxy 6-hydroxyhexanoate, 1,1-dimethylpropylperoxy 8-hydroxyoctanoate, 3-hydroxy-1,1-dimethylbutylperoxy 12-hydroxylauroate, 3-hydroxy-1,1-dimethylbutylperoxy 10-hydroxydecanoate, 3-hydroxy-1,1-dimethylbutylperoxy 6-hydroxyhexanoate, 3-hydroxy-1,1-dimethylbutylperoxy 4-(hydroxymethyl)benzoate; and hydroxydiacylperoxides such as 2,5-dimethyl-2,5-di(6-hydroxyhexanoylperoxy) hexane, 1,3-di(1-methyl-1-(5-hydroxypentanoylperoxy)ethyl)cyclohexane, di(3-hydroxybutanoyl) peroxide di(4-hydroxybutanoyl)peroxide, di(2-hydroxypentanoyl)peroxide, di(3-hydroxypentanoyl) peroxide, di(4-hydroxypentanoyl)peroxide, di(5-hydroxypentanoyl)peroxide, di(hydroxyethanoyl)peroxide, di(2-hydroxyisobutanoyl)peroxide, di(2-hydroxypropanoyl) peroxide, di(2-hydroxyhexanoyl)peroxide, di(6-hydroxyhexanoyl)peroxide, di(8-hydroxyoctanoyl) peroxide, di(hydroxypivaloyl)peroxide, di(12-hydroxylauroyl)peroxide, di(10-hydroxydecanoyl)peroxide, di(4-(hydroxymethyl)benzoyl)peroxide, 6-carboxyhexaneperoxoic acid OO-(1,1-dimethylethyl) O-(4-hydroxybutyl)ester, bis(6-(4-hydroxybutyloxy)-6-oxohexanoyl peroxide, benzenecarboperoxoic acid 2-carboxy OO-(3-hydroxy-1,1-dimethylbutyl) O-(6-hydroxyhexyl)ester, and bis(2-(6-hydroxyhexyloxycarbonyl)benzoyl) peroxide.

Preferably, the hydroxyperester in accordance with the present invention is selected from the group consisting of tert-butylperoxy 6-hydroxyhexanoate, tert-amylperoxy 6-hydroxyhexanoate, 3-hydroxy-1,1-dimethylbutylperoxy 6-hydroxyhexanoate, 3-(2-hydroxyethoxy)-1,1-dimethylbutylperoxy 6-hydroxyhexanoate, tert-butylperoxy 3-hydroxybutanoate, tert-amylperoxy 3-hydroxybutanoate, 3-hydroxy-1,1-dimethylbutylperoxy 3-hydroxybutanoate, and 3-(2-hydroxyethoxy)-1,1-dimethylbutylperoxy 3-hydroxybutanoate. More preferably, the group consisting of tert-butylperoxy 6-hydroxyhexanoate, tert-amylperoxy 6-hydroxyhexanoate, and 3-(2-hydroxyethoxy)-1,1-dimethylbutylperoxy 6-hydroxyhexanoate.

Preferably, the hydroxydiacylperoxide in accordance with the present invention is selected from the group consisting of di(6-hydroxyhexanoyl)peroxide and di(3-hydroxybutanoyl) peroxide.

Reaction Conditions

The process of the invention is carried out using means and equipment known to a person of ordinary skill in the art. It can be carried out in a batch, semi-batch or continuous fashion.

The process according to the present invention can be carried out in the presence or absence of an added reaction medium. It may be performed in an aqueous medium, in a mixture of water and an organic solvent, in an organic solvent, or in the absence of any water and organic solvent. In this last case, the mixed anhydride and the hydroperoxide react with each other in the absence of any added reaction medium, i.e. neat. Typical suitable solvents include ethers such as diethyl ether, esters, and optionally halogenated alkanes. Preferably, no organic solvent is used in the process according to the present invention, most preferably the reaction is carried out in an aqueous medium.

This most preferred embodiment has the advantage that no organic solvent is used. In addition, the organic phase can easily be separated from the aqueous phase using conventional separation techniques.

A further advantage is that the peroxide which is prepared in an aqueous medium can easily be transformed into an emulsion or suspension of the peroxide without separating the organic layer containing the peroxide from the water layer. This formulation then can be used directly in one or more of the above-described applications.

During the reaction one or, in the case of a di-, tri- or tetravalent $R^1$ group or a divalent $R^5$ group, more equivalents of a carbonate of formula $^-OC(O)OR^2$ or $[^-OC(O)O]_pR^4$ are formed. When for example an aqueous sodium hydroxide solution is used as the base in the invention process (see below), the corresponding sodium carbonate is formed. This carbonate can be removed from the reaction mixture, i.e. the reaction products, by washing with water. If a pH lower than 7 is used for the reaction, the carbonate of formula $^-OC(O)OR^2$ or $[^-OC(O)O]_pR^4$ typically decomposes to form the corresponding (di)alcohol and carbon dioxide. The preferred chloroformates yield alcohols which can be removed from the organic phase containing the peroxide by washing.

The invention process can be carried out within a wide range of molar ratios of mixed anhydride to hydroperoxide. Preferably, a small molar excess of hydroperoxide is used, i.e. typically 1 to 40, preferably 2 to 20 mole %.

Any base can be used for making the peracid, perester or diacylperoxide in accordance with the process of the present invention. Suitable bases include alkali metal hydroxides such as lithium hydroxide, sodium hydroxide, and potassium hydroxide, alkaline earth metal hydroxides such as magnesium hydroxide and calcium hydroxide, sodium carbonate, sodium bicarbonate, sodium phosphate, sodium hydrogen phosphate, calcium oxide, magnesium oxide, and amines like pyridine, trimethylamine, and triethylamine, and mixtures thereof, alkali metal hydroxides being preferred. Preferably, sodium hydroxide, potassium hydroxide, sodium carbonate, sodium phosphate, pyridine, trimethylamine, triethylamine or a mixture thereof, more preferably sodium hydroxide, potassium hydroxide, sodium carbonate, sodium phosphate or a mixture thereof, most preferably sodium hydroxide or potassium hydroxide is used. Typically, an aqueous solution of the base is used in the invention process.

Typically, the pH is kept at a value of 4 or higher, preferably 5 or higher, more preferably 6 or higher, most preferably 10 or higher.

The process according to the invention can be performed within a wide temperature range, typically of −25 to 75° C. The reaction temperature is determined by the decomposition temperature of the peroxide formed during the process of the invention and the reactivity of the mixed anhydride and the hydroperoxide. Preferably, the reaction is carried out at a temperature in the range of −5 to 50° C., most preferably 0 to 30° C.

The invention process typically is performed at atmospheric pressure.

Typically, the reaction time varies from 0.05 to 10 h. A suitable reaction time is from 0.5 to 4 h.

In a typical procedure, to a reaction vessel equipped with a turbine stirrer, a thermometer and a pH electrode/pH meter are added water—optionally containing sodium chloride, which may increase the yield of the reaction-, the carboxylic acid, and optionally a quaternary ammonium phase transfer catalyst. The temperature and the pH are adjusted to the desired values—the pH preferably by dosing an aqueous sodium hydroxide solution. Then, the halogen formate and the base—preferably an aqueous sodium hydroxide solution—are added—preferably simultaneously—over a certain period of time while the temperature and the pH are kept at the desired values. After completion of the formation of the mixed anhydride, the hydroperoxide is added with control of the temperature and the pH. The reaction is allowed to proceed until about all of the mixed anhydride has reacted.

The work-up procedure depends on the type of peroxide being prepared. For peresters, the water layer is separated from the organic layer containing the peroxide and the organic layer is subsequently washed with an aqueous sodium sulphite solution, water, and/or an aqueous sodium chloride solution and then dried. In the case of diacylperoxides, the water layer is separated from the organic layer, e.g., by liquid/liquid separation or filtration, and the organic layer is washed with water and/or an aqueous sodium chloride solution and, in the case of a liquid peroxide, dried. For peracids, the water layer is acidified, and the organic layer is separated from the water layer, e.g., by liquid/liquid separation or filtration, washed with water and/or an aqueous sodium chloride solution, and then dried. Solid peroxides are isolated by filtration or centrifugation and may be recrystallized from a suitable solvent.

Typically, the nucleophilic attack of the hydroperoxide on the carboxylic acid carbonyl group of the mixed anhydride is not completely selective. As shown in the examples below, which are non-optimized experiments, yields typically range between 70 and 86%. Without wishing to be bound by any theory, Applicant believes that the selectivity is determined by steric hindrance and the inductive effects on the carboxylic acid and formic acid carbonyl groups, and that it can be steered to some extent by the appropriate selection of R groups. It was found that the best results in terms of yield and selectivity were obtained using isopropyl chloroformate and sec-butyl chloroformate.

The peracids, peresters, diacylperoxides, and hydroxyperoxides in accordance with the present invention may be formulated in a conventional way. To this end, the reader is referred to the state of the art, for example WO 99/32442.

The peroxides obtained by the process according to the present invention can be used in all applications mentioned above, e.g., the polymerization of monomers and/or the modification of these polymers and other polymers as described above, in the usual amounts and using conventional methods.

The hydroxyperesters and hydroxydiacylperoxides obtainable by the process of this invention are particularly suitable for use in (co)polymer modification reactions, e.g. the preparation of hydroxy-functionalized poly(meth) acrylates. Said acrylates may be used for example in high solids coating resins.

The present invention is illustrated by the following examples.

EXAMPLES

The reactions were monitored by means of thin-layer chromatography, capillary gas chromatography (GC) (Chrompack CP Sil 5 CB MS column, hydrogen carrier gas, FID detection), $^{13}$C-NMR, $^{1}$H-NMR, and/or Fourier transform infrared (FT-IR) spectroscopy.

Preparation of Peroxides

Example 1 tert-Butylperoxy 2-Ethylhexanoate

To a well-stirred reaction vessel equipped with a thermometer and a pH electrode were added 35 g of a 25 wt % aqueous solution of NaCl and tert-butyl hydroperoxide (TBHP) (0.069 mole, 70 wt % aqueous solution) at 5° C. The pH was adjusted to 12 using a 33 wt % aqueous NaOH solution. Then, 2-ethylhexanoyl 1-methyl-1-propyl carbonate (0.062 mole) was dosed within 30 min with the temperature being kept at 5° C. and the pH at 12. During a post-reaction period of 120 min at 5° C. the pH was kept between 12 and 13. The water layer was separated, and the organic product layer was washed with a 2 wt % aqueous $NaHSO_3$ solution and subsequently with a 1 wt % aqueous $NaHCO_3$ solution. After drying over $MgSO_4$ and filtration, 13.9 g of tert-butylperoxy 2-ethylhexanoate having a content of 80% were obtained in a yield of 81%. The molar ratio of tert-butylperoxy 2-ethylhexanoate to tert-butylperoxy 1-methyl-1-propyl carbonate was calculated to be 91.5:8.5.

Example 2 tert-Butylperoxy 4-Methoxyphenoxyacetate

To a well-stirred reaction vessel equipped with a thermometer and a pH electrode were added 2-(4-methoxyphenoxy)acetyl 1-methyl-1-propyl carbonate (0.012 mole), 20 ml of diethyl ether, and 20 ml of a 25 wt % aqueous NaCl solution. The reaction mixture was cooled to below 10° C. and the pH was increased to a value above 11 using a 25 wt % aqueous NaOH solution. Then, TBHP (0.013 mole) was dosed with this temperature and pH being maintained. The mixture was post-reacted for 90 min at a temperature between 0 and 10° C. and a pH of above 11. Working up was as described in Example 1. After evaporation of the diethyl ether, 2.3 g of tert-butylperoxy 4-methoxyphenoxyacetate (an orange oil) having a content of 92.5% were obtained in a yield of 70%.

Example 3 tert-Butylperoxy 2-Methylbenzoate

Following the same procedure as described in Example 2, but using 2-methylbenzoyl 1-methyl-1-propyl carbonate, tert-butylperoxy 2-methylbenzoate having a content of 89% was obtained in a yield of 80%.

Example 4 tert-Butylperoxy 3-Chlorobenzoate

To a well-stirred reaction vessel equipped with a thermometer and a pH-electrode were added 39 g of water and 0.20 g of Arquad CB50 at 5° C. After the addition of 0.05 mole of 3-chlorobenzoic acid the pH was adjusted to 6 using a 10 wt % aqueous NaOH solution. Then, 0.05 mole of sec-butyl chloroformate was dosed within 5 min at 5° C. During this time and a post-reaction time of 165 min at 5° C. the pH was kept at a value between 6 and 9. After the post-reaction, 8.1 g of TBHP were added (0.063 mole), and using a 33 wt % aqueous NaOH solution the pH was adjusted to 13 within 5 min while keeping the temperature at 5° C. During a post-reaction time of 75 min at 5° C. the pH was maintained at 13. Then, 25 g of diethyl ether were added, and the reaction mixture was allowed to separate. After separation of the water layer, the organic layer was washed, twice with 40 g of a 15 wt % aqueous NaCl solution. The ether layer was dried over $MgSO_4$, and the diethyl ether was removed under vacuum. As a result, 9.4 g of tert-butylperoxy 3-chlorobenzoate having a content of 95.4% were obtained in a yield of 80% based on 3-chlorobenzoic acid. The molar ratio of tert-butylperoxy 3-chlorobenzoate to tert-butylperoxy 1-methyl-1-propylcarbonate was calculated to be 97.6:2.4.

Example 5

Dicyclohexylcarbonylperoxide

To a well-stirred reaction vessel equipped with a thermometer and a pH electrode were added 30 g of an 8 wt % aqueous $Na_2CO_3$ solution and $H_2O_2$ (0.0270 mole, 70 wt % aqueous solution) at 5° C. The pH was adjusted to 12 using a 33 wt % aqueous NaOH solution. Then, cyclohexylcarbonyl 1-methyl-1-propyl carbonate (0.050 mole) was dosed within 5 min with the temperature being kept at 5° C. and the pH at 12. During a post-reaction time of 80 min at 5° C. the pH was kept at 12. After the addition of diethyl ether, the reaction mixture was allowed to separate. After removal of the diethyl ether, 5.9 g of dicyclohexylcarbonylperoxide having a content of 93% were obtained in a yield of 86%. The molar ratio of dicyclohexylcarbonylperoxide to cyclohexanoyl 1-methyl-1-propyl carbonate was calculated to be 90:10.

Preparation of Mixed Anhydrides

Example 6

2-Ethylhexanoyl Methyl Carbonate

To a well-stirred reaction vessel equipped with a thermometer and a pH electrode were added 45 g of water, 0.075 mole of a 33 wt % aqueous NaOH solution, 0.075 mole of 2-ethylhexanoic acid, and 0.23 g of Arquad CB50 (i.e. cocobenzyldimethylammonium chloride, ex Akzo Nobel) at 5° C. 0.075 mole of methyl chloroformate was dosed in 5 min at 5° C. The mixture was post-reacted for 30 min at 5° C. and a pH of 8. Then, the water layer was separated, giving 15.2 g of 2-ethylhexanoyl methyl carbonate having a content of 99.5% (determined by NMR) in a yield of 99.6%.

Example 7

2-Ethylhexanoyl Methyl Carbonate

Following the same procedure as described in Example 6, but without using the quaternary ammonium phase transfer catalyst and with a post-reaction time of 100 min, 11.9 g of 2-ethylhexanoyl methyl carbonate having a content of 78% were obtained in a yield of 61%.

Example 8

2-Ethylhexanoyl 1-Methyl-1-Propyl Carbonate

Following the same procedure as described in Example 6, but using 0.075 mole of sec-butyl chloroformate, a post-reaction time of 125 min, and a pH during dosing and post-reaction of 8.5, 18.0 g of 2-ethylhexanoyl 1-methyl1-propyl carbonate having a content of 99% were obtained in a yield of 97%.

Example 9

2-Ethylhexanoyl Phenyl Carbonate

Following the same procedure as described in Example 6, but using 0.075 mole of phenyl chloroformate and a post-reaction time of 40 min, 19.7 g of 2-ethylhexanoyl phenyl carbonate having a content of 83% were obtained in a yield of 82%.

Example 10

2-Ethylhexanoyl 2-Ethylhexyl Carbonate

Following the same procedure as described in Example 6, but using 0.075 mole of 2-ethylhexyl chloroformate, a post-reaction time of 185 min, and a pH during dosing and post-reaction of between 8 and 9, 22.6 g of 2-ethylhexanoyl 2-ethylhexyl carbonate having a content of 97.9% were obtained in a yield of 98%.

Example 11

3-Chlorobenzoyl 1-Methyl-1-propyl Carbonate

To a well-stirred reaction vessel equipped with a thermometer and a pH electrode were added 39 g of water and 0.20 g of Arquad CB50 at 5° C. After the addition of 0.05 mole of 3-chlorobenzoic acid the pH was adjusted to 6 using a 10 wt % aqueous NaOH solution. Then, 0.05 mole of sec-butyl chloroformate was dosed within 5 min at 5° C. During this time and a post-reaction time of 165 min at 5° C. the pH was kept at a value between 6 and 9. The reaction mixture was allowed to separate, giving 12.5 g of 3-chlorobenzoyl 1-methyl-1-propyl carbonate having a content of 98% in a yield of 95%.

Example 12

Acetyl 1-Methyl-1-propyl Carbonate

Following the same procedure as described in Example 10, but using 0.05 mole of acetic acid, a pH during dosing and post-reaction of 6, and a post-reaction time of 120 min, 5.5 g of acetyl 1-methyl-1-propyl carbonate having a content of 70% were obtained in a yield of 50%.

Example 13

Phenoxyacetyl 1-Methyl-1-propyl Carbonate

To a well-stirred reaction vessel equipped with a thermometer and a pH electrode were added 100 ml of diethyl ether, 40 ml of a 25 wt % aqueous NaCl solution, and 0.4 g of Arquad CB50. After cooling the reaction mixture to 5–10° C., 0.066 mole of phenoxy acetic acid was added. The pH was adjusted to a value between 6 and 7 using a 25 wt % aqueous NaOH solution. Then, 0.066 mole of sec-butyl chloroformate was dosed within 5 min at 5–10° C. During this time and a post-reaction time of 40 min at 5–10° C. the pH was kept at 6–7. The reaction mixture was allowed to separate. After removal of the diethyl ether, 15 g of phenoxyacetyl 1-methyl-1-propyl carbonate having a content of 90% were obtained in a yield of 81%.

Preparation of Hydroxyperoxides

Example 14 di(6-Hydroxyhexanoyl)peroxide

To a well-stirred reaction vessel equipped with a thermometer and a pH electrode were added 34.3 g of 6-hexanolactone, 20 g of water, and 48 g of a 25 wt % aqueous NaOH solution. The reaction mixture was stirred for 30 min while cooling down slowly. The sodium 6-hydroxyhexanoate solution formed was cooled to 4° C. and to this solution 130 mg of N-methylmorpholine was added. Then, 34 g of isopropyl chloroformate was added in 2 min. The reaction mixture was stirred for 90 min at 10° C. Chloroformate level in the organic layer was low and mixed anhydride was formed according to analysis by FT-IR. To this reaction mixture, 6.5 g of a 70 wt % aqueous $H_2O_2$ Solution was added with stirring and the temperature was kept at 10° C. for 120 min. The pH was kept at 6–7 by addition of 3 g of a 25 wt % aqueous NaOH solution. The white solid formed was filtered and washed with 300 g of cold water. Vacuum drying of the solid resulted in 29 g of di(6-hydroxyhexanoyl)peroxide with an active content of 86% in a yield of 68%.

Example 15 di(3-Hydroxybutanoyl)peroxide

To a well-stirred reaction vessel equipped with athermometer and a pH electrode were added 19.8 g of ethyl 3-hydroxybutanoate, 8 g of water, and 24.4 g of a 25wt % aqueous NaOH solution. The mixture was stirred for 120 min while cooling down slowly. The sodium 3-hydroxybutanoate solution was cooled to 5° C. and to this solution 90 mg of N-methylmorpholine was added. Then, 16,8 g of isopropyl chloroformate was added in 1 min. The reaction mixture was stirred for 30 min at 5° C. Chloroformate level in the organic layer was low and mixed anhydride was formed according to analysis by FT-IR. To this reaction mixture, 3.1 g of a 70 wt % aqueous $H_2O_2$ solution was added with stirring in 4 min and the temperature was kept at 5° C. for 90 min. The pH was kept at 6–7 by the addition of 2 g of a 25 wt % aqueous NaOH solution. Diethyl ether was added to the reaction mixture and the water phase was separated. The ether layer was washed with 20 g of a 25 wt % aqueous NaCl solution and then was dried with $MgSO_4$. After removal of the ether in vacuum at 10° C. a viscous colourless liquid was obtained with a diacylperoxide content of 75% and in a yield of 62% based on the starting ester.

Example 16 tert-Butylperoxy 6-Hydroxyhexanoate

To a well-stirred reaction vessel equipped with a thermometer and a pH electrode were added 17.1 g of 6-hexanolactone, 16 g of water, and 24 g of a 25 wt % aqueous NaOH solution. The mixture was stirred for 30 min while cooling down slowly. The sodium 6-hydroxyhexanoate solution formed was cooled to 4° C. and to this solution 70 mg of N-methylmorpholine was added. Then, 16.2 g of isopropyl chloroformate was added in 2 min. The reaction mixture was stirred for 90 min at 10° C. Chloroformate level in the organic layer was low and mixed anhydride was formed according to analysis by FT-IR. The water layer was separated and 19.3 g of a 70 wt % aqueous tert-butyl hydroperoxide solution (ex Lyondell) was added. With stirring, 0.5 g of $Na_2CO_3$ was added and 12.5 g of a 25 wt % aqueous NaOH solution was dosed in 20 min at 10° C. The reaction mixture was stirred for 60 min at 10° C. For a fast layer separation some water and diethyl ether were added. The water layer was separated and the organic layer was extracted with an aqueous sodium sulfite solution in order to reduce all hydroperoxide present. The organic layer was washed with an aqueous $NaHCO_3$ solution to a neutral pH and the product was dried over $MgSO_4$. After removal of the ether in vacuum at 20° C. a colourless liquid was obtained with a perester content of 92% in a yield of 62% based on the starting chloroformate.

Example 17 tert-Amylperoxy 6-Hydroxyhexanoate

Following the procedure of Example 16 described above, but using 18.3 g of an aqueous 85 wt % tert-amyl hydroperoxide solution (ex Akzo Nobel), a product with a perester content of 87% in a yield of 58% was obtained.

Example 18

3-Hydroxy-1,1-dimethylbutylperoxy 6-Hydroxyhexanoate

Following the procedure of Example 16 described above, but using 23.0 g of 3-hydroxy-1,1-dimethylbutyl hydroperoxide (51 wt % in toluene, ex Akzo Nobel), Arquad CB50 (cocobenzyldimethylammonium chloride, ex Akzo Nobel) as a catalyst, and extracting the water layers with toluene, a product with a perester content of 86% in a yield of 51% was obtained.

Use of Hydroxyperoxides in the Production of High Solids Acrylate Resins

Example 19 di(6-Hydroxyhexanoyl)peroxide

A mixture of 40 g butyl acrylate, 28 g of ethyl methacrylate, 20 g of styrene, 10 g of methyl methacrylate, and 2 g of methacrylic acid was polymerized in 40 g of butyl acetate at 100° C. in a conventional way using 15 mmoles of di(6-hydroxyhexanoyl)peroxide/100 g monomers. Conventional analysis of the resulting polymer gave the following results: a solids content of 60.8%, Mw of 28.700, Mn of 12.600, and Mw/Mn of 2.3. The resin was found to contain hydroxy groups.

Example 20

3-Hydroxy-1,1-dimethylbutylperoxy 6-Hydroxyhexanoate

A mixture of 40 g butyl acrylate, 28 g of ethyl, methacrylate, 20 g of styrene, 10 g of methyl methacrylate, and 2 g of methacrylic acid was polymerized in 40 g of butyl acetate at 126° C. in a conventional way using 30 mmoles of 3-hydroxy-1,1-dimethylbutylperoxy 6-hydroxyhexanoate/100 g of monomers. Conventional analysis of the resulting polymer gave the following results: a solids content of 70.4%, Mw of 10.500, Mn of 5.330, and Mw/Mn of 2.0. Analysis showed that the resin was functionalized with hydroxy groups.

We claim:

1. A process for preparing a perester, characterized in that a mixed anhydride of formula $R^1[C(O)OC(O)OR^2]_n$ or $[R^3C(O)OC(O)O]_pR^4$ is contacted with a hydroperoxide of formula $R^5[OOH]_m$ in the presence of a base, wherein $R^1$ represents a mono-, di-, tri- or tetrasubstituted $C_1$–$C_{19}$ hydrocarbon group, optionally containing one or more hetero atoms, n in 1–4, $R^2$ represents a $C_1$–$C_{20}$ hydrocarbon group, optionally containing one or more hetero atoms, $R^3$ represents a $C_1$–$C_{19}$ hydrocarbon group, optionally containing one or more hetero atoms, $R^4$ represents a di-, tri- or tetrasubstituted $C_1$–$C_{20}$ hydrocarbon group, optionally containing one or more hetero atoms, p is 2–4, $R^5$ represents hydrogen or a mono- or disubstituted $C_3$–$C_{18}$ tertiary alkyl or $C_2$–$C_{20}$ acyl group, in which the tertiary alkyl or acyl group may optionally contain one or more hetero atoms, m is 1 or 2, and if $R^5$ represents hydrogen, m is 1, provided that if the hydroperoxide is an α,α'-dihydroperoxyperozide, the reaction is not carried out in an inert two-phase solvent system comprising a polar solvent and an apolar solvent.

2. The process of claim 1 wherein n is 1 or 2.

3. The process of claim 1 wherein $R^1$ and $R^3$ each independently represents a linear or branched $C_4$–$C_{12}$ alkyl or $C_6$–$C_{12}$ aryl group, said alkyl and aryl groups optionally being substituted with a hydroxy group, a linear or branched $C_1$–$C_4$ alkyl group or a halogen atom.

4. The process of claim 1 wherein $R^2$ is selected from a $C_3$–$C_8$ alkyl group or a $C_6$–$C_{12}$ aryl group.

5. The process of claims 1 wherein said mixed anhydride is a mixed anhydride of the formula $R^1[C(O)OC(O)OR^2]$ wherein $R^1$ is selected from mono-, di-, tri- or tetravalent $C_1$–$C_{19}$ hydrocarbon group, optionally containing one or more hetero atoms, and $R^2$ is selected from a $C_1$–$C_{20}$ hydrocarbon group, optionally containing one or more hetero atoms.

6. The process of claim 1 wherein $R^5$ represents hydrogen or a monovalent $C_3$–$C_{18}$ tertiary alkyl group.

7. The process of claim 1 wherein the base is an alkali metal hydroxide.

8. The process of claim 1 wherein the reaction is carried out at a pH of 5 or higher.

9. The process of claim 1 wherein the reaction is carried out in the absence of an organic solvent.

10. The process of claim 1 wherein the mixed anhydride is prepared by contacting a carboxylic acid of formula $R^1[C(O)OH]_n$ with a halogen formate of formula $XC(O)OR^2$ or $[XC(O)O]_pR^4$ in the presence of a base in an aqueous medium, wherein $R^1$, $R^2$, $R^4$, n, and p have the same meaning as defined in claim 1 and X is a halogen atom.

11. The process of claim 10 wherein a quaternary ammonium phase transfer or tertiary amine catalyst is present.

12. A hydroxyperester selected from the group consisting of tert-butylperoxy 6-hydroxyhexanoate, tert-amylperoxy 6-hydroxyhexanoate, 3-(2-hydroxyethoxy)-1,1-dimethylbutylperoxy 6-hydroxyhexanoate, tert-butylperoxy 3-hydroxybutaneate, tert-amylperoxy 3-hydroxybutanoate, 3-hydroxy-1,1-dimethylbutylperoxy 3-hydroxybutanoate, 3(2-hydroxyethoxy)-1,1-dimethylbutylperoxy 3-hydroxybutanoate, 3-hydroxy-1,1-dimethylbutylperoxy 4-hydroxybutanoate, 1,1-dimethylpropylperoxy 3-hydroxypentanoate, 1,1,4,4-tetramethylbutylperoxy 4-hydroxypentanoate, 3-hydroxy-1,1,-dimethylbutylperoxy 5-hydroxypentanoate, cumylperoxy 6-hydroxyhexanoate, 1,1-dimethylpropylperoxy 8-hydroxyoctanoate, 3-hydroxy-1,1-dimethylbutylperoxy 12-hydroxylauroate, 3-hydroxy-1,1-dimethylbutylperoxy 10-hydroxydecanoate, 3-hydroxy-1,1-dimethylbutylperoxy 6-hydroxyhexanoate, and 3-hydroxy-1,1-dimethylbutylperoxy 4-(hydroxymethyl)benzoate.

* * * * *